(12) United States Patent
Wang (10) Patent No.: US 7,869,044 B2
(45) Date of Patent: Jan. 11, 2011

(54) OPTICAL SENSING SYSTEM BASED ON A MICRO-ARRAY STRUCTURE

(75) Inventor: Hong Wang, Cupertino, CA (US)

(73) Assignee: OptoTrace Technologies, Inc., Mountain View, CA (US)

( * ) Notice: Subject to any disclaimer, the term of this patent is extended or adjusted under 35 U.S.C. 154(b) by 337 days.

(21) Appl. No.: 12/014,800

(22) Filed: Jan. 16, 2008

(65) Prior Publication Data

US 2009/0180112 A1    Jul. 16, 2009

(51) Int. Cl.
*G01N 21/00* (2006.01)

(52) U.S. Cl. .................. 356/432; 356/436; 356/440; 435/7.92

(58) Field of Classification Search ......... 356/432–440, 356/301, 326, 327, 244, 246; 435/288.4, 435/288.5, 287.9
See application file for complete search history.

(56) References Cited

U.S. PATENT DOCUMENTS

| 5,581,091 | A | 12/1996 | Moskovits | |
|---|---|---|---|---|
| 5,864,397 | A | 1/1999 | Vo-Dinh | |
| 6,231,744 | B1 | 5/2001 | Ying | |
| 6,361,681 | B1 | 3/2002 | Gao | |
| 6,464,853 | B1 | 10/2002 | Iwasaki | |
| 6,614,523 | B1 | 9/2003 | Boss | |
| 7,364,696 | B1 * | 4/2008 | Sarvazyan | 422/61 |
| 7,463,357 | B2 * | 12/2008 | Kralik et al. | 356/417 |
| 7,483,130 | B2 * | 1/2009 | Baumberg et al. | 356/301 |
| 2002/0015147 | A1 * | 2/2002 | Maher et al. | 356/139.1 |
| 2002/0109835 | A1 * | 8/2002 | Goetz | 356/237.1 |
| 2002/0182970 | A1 | 12/2002 | Liu | |
| 2002/0187260 | A1 * | 12/2002 | Sheppard et al. | 427/248.1 |
| 2003/0010808 | A1 * | 1/2003 | Uhland et al. | 228/110.1 |
| 2003/0105455 | A1 * | 6/2003 | Santini et al. | 604/890.1 |
| 2003/0175472 | A1 | 9/2003 | Den | |
| 2005/0100974 | A1 * | 5/2005 | Duffy et al. | 435/7.92 |
| 2005/0280832 | A1 * | 12/2005 | Johnson et al. | 356/625 |
| 2009/0163895 | A1 * | 6/2009 | Ausiello et al. | 604/891.1 |

* cited by examiner

*Primary Examiner*—Hoa Q Pham
(74) *Attorney, Agent, or Firm*—Xin Wen (57) ABSTRACT

An optical sensing system includes an optical sensor that includes a substrate having an upper surface and a plurality of tapered walls on the substrate, wherein at least one of the tapered walls is aligned along a longitudinal direction, wherein the plurality of tapered walls comprise sloped surfaces oriented at oblique angles relative to the upper surface, wherein the sloped surfaces are configured to adsorb molecules of a chemical sample, a light source configured to emit an incident light beam to impinge the plurality of tapered walls adsorbed with molecules of the chemical sample; and a detector that can collect light scattered by the plurality of tapered walls to allow a determination of the sample chemical.

21 Claims, 10 Drawing Sheets

OPTICAL SENSING SYSTEM BASED ON A MICRO-ARRAY STRUCTURE

BACKGROUND

The present application relates to optical sensing systems for detecting chemicals and biological agents.

Optical sensing systems have been used for detecting chemicals and biological agents. In such detection techniques, chemical molecules to be detected are adsorbed on the surfaces of an optical sensor. An incident light beam such as a laser beam illuminates the sensing surfaces adsorbed with the molecules. The incident light beam is scattered by the surfaces. The scattered light is collected and used to determine the identity of the chemical.

A challenge to the optical sensing technique is that the intensity of the scattered light is often too weak for identifying low concentration level of chemicals, which limits the application of the optical sensing techniques for detecting chemicals. For example, it is difficult to reliably detect trace level of chemicals in the field using optical sensing techniques. Trace chemical detection usually needs to be carried out in a wet laboratory.

SUMMARY

In a general aspect, the present application relates to a micro structure including an optical sensing system that includes an optical sensor that includes a substrate having an upper surface and a plurality of tapered walls on the substrate, wherein at least one of the tapered walls is aligned along an longitudinal direction, wherein the plurality of tapered walls comprise sloped surfaces oriented at oblique angles relative to the upper surface, wherein the sloped surfaces are configured to adsorb molecules of a chemical sample; a light source configured to emit an incident light beam to impinge the plurality of tapered walls adsorbed with molecules of the chemical sample; and a detector that can collect light scattered by the plurality of tapered walls to allow a determination of the sample chemical.

In another general aspect, the present application relates to a micro structure including an optical sensing system including an optical sensor including a substrate having an upper surface and a plurality of tapered walls on the substrate, wherein the plurality of tapered walls comprise sloped surfaces oriented at oblique angles relative to the upper surface of the substrate, wherein at least two adjacent tapered walls define therein an air gap having a width that varies as a function of a distance from the upper surface; a light source configured to emit an incident light beam to impinge the plurality of tapered walls adsorbed with molecules of a chemical sample; and a detector that can collect light scattered by the plurality of tapered walls to allow a determination of the sample chemical.

In another general aspect, the present application relates to a method for detecting chemicals or biological sample. The method includes forming a adsorbing molecules of the chemical or biological sample on surfaces of the plurality of tapered walls on a substrate in an optical sensor, wherein at least one of the tapered walls is aligned along an longitudinal direction; illuminating the plurality of tapered walls by an incident light beam at a predetermined angle relative to the plurality of tapered walls; forming a scattered light by the plurality of tapered walls adsorbed with the molecules of the chemical or biological sample; and determining identity of the chemical or biological sample chemical using the scattered light.

In another general aspect, the present application relates to a method for fabricating an optical sensor. The method includes forming a mask layer on an upper surface of a substrate; forming a plurality of openings in the mask layer to expose portions of the upper surface of the substrate, wherein two adjacent openings in the mask layer have their respective centers at a distance between about 5 nanometers and about 200 micrometers; removing material in the substrate through the openings in the mask layer to form a plurality of recesses each having a sloped surface; removing the mask layer from the upper surface of the substrate to form a plurality of tapered walls on the substrate, wherein two adjacent tapered walls define therein an air gap having a width that varies as a function of a distance from the upper surface, wherein the width of the air gap is in a range from 0 to about 200 micrometers; and depositing a conductive material on the plurality of tapered walls.

Implementations of the system may include one or more of the following. At least two of the plurality of tapered walls can be substantially parallel to each other. The incident light beam can be substantially perpendicular to the longitudinal direction of at least one of the tapered walls. The incident light beam can be substantially parallel to the longitudinal direction of at least one of the tapered walls. The incident light beam can be at an oblique angle relative to the longitudinal direction of at least one of the tapered walls. The incident light beam can have a linear polarization substantially parallel to the longitudinal direction of at least one of the tapered walls. The incident light beam can have a linear polarization at an oblique angle relative to the longitudinal direction of at least one of the tapered walls. The optical sensing system can further include a transport system configured to move the optical sensor to a position to allow the incident light beam to impinge on the plurality of tapered walls. The optical sensing system can further include a device configured to deliver the chemical sample to the optical sensor. The plurality of tapered walls in the optical sensor can include varying dimensions matching the mean free paths or wavelength of excited electrons or the wavelength of phonons excited by the incident light beam. At least one of the plurality of tapered walls in the optical sensor can be formed unitarily with the substrate in the optical sensor. At least one of the tapered walls in the optical sensor can have a length between about 2 nanometers and about 100 millimeters, a height between about 0.5 nanometers and about 200 micrometers, and a base having widths in a range of about 1 nanometer and about 200 micrometers. At least one of the plurality of tapered walls in the optical sensor can include a first sloped surface at an angle between about 5 degrees and about 85 degrees relative to the upper surface of the substrate and a top portion in part defined by the first sloped surface, wherein two adjacent tapered walls have their respective top portions at a first distance between about 2 nanometers and about 200 micrometers and their respective bases at a second distance smaller than 200 micrometers. The first sloped surface can be at an angle between about 10 degrees and about 80 degrees relative to the upper surface of the substrate. Two adjacent tapered walls can have their respective bases in contact or joining with each other. The top portion in the one of the plurality of tapered walls can include a top surface substantially parallel to the upper surface of the substrate. The top portion in the one of tapered walls can include a ridge substantially parallel to the longitudinal direction. At least one of the tapered walls can include a second sloped surface at an oblique angle relative to the upper surface of the substrate. The substrate can include a material selected from the group consisting of silicon, $TiO_2$, $SiO_2$, $Al_2O_3$, $Si_3N_4$, $Ta_2O_5$, Zn oxide, Sn oxide, Sb oxide, Ag oxide, Au oxide, Ethylene Chlorotrifluoroethylene (ECTFE), Poly(ethylene-co-butyl acrylate-co-carbon monoxide) (PEBA), Poly (allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP). At least one of the plurality of tapered walls can include a conductive material on the sloped surfaces. The conductive material can be selected from the group consisting of Ag, Au, Cu. Pt, Al, Fe, Co, Ni, Ru, Rh, Pd, Ag doped with chlorine or chloride, and Au doped with chlorine or chloride.

Embodiments may include one or more of the following advantages. The disclosed systems and methods can increase the signal intensities in defecting chemicals using optical sensing techniques. The disclosed optical sensing systems and methods allow optical sensing techniques to be more widely applied in chemical detection. The disclosed system and methods can reliably detect trace amount of chemicals or biological agents in real time and in the field. The disclosed system and methods allow trace chemical detection using portable optical sensing devices, which can enable chemical detection to be conveniently implemented at locations such as security gates at airports for detecting explosive materials, grocery stores for monitoring food contamination or agriculture residue chemicals on food, and doctors' office for diagnostic tests. The disclosed optical sensing systems and methods can also allow the detection a number of chemicals and biological agents using a single optical sensor.

These and other objects and advantages of the present, application will become obvious to those of ordinary skill in the art after having read the following detailed description of the preferred embodiment, which is illustrated in the various drawing figures.

DETAILED DESCRIPTION

Figure 1:
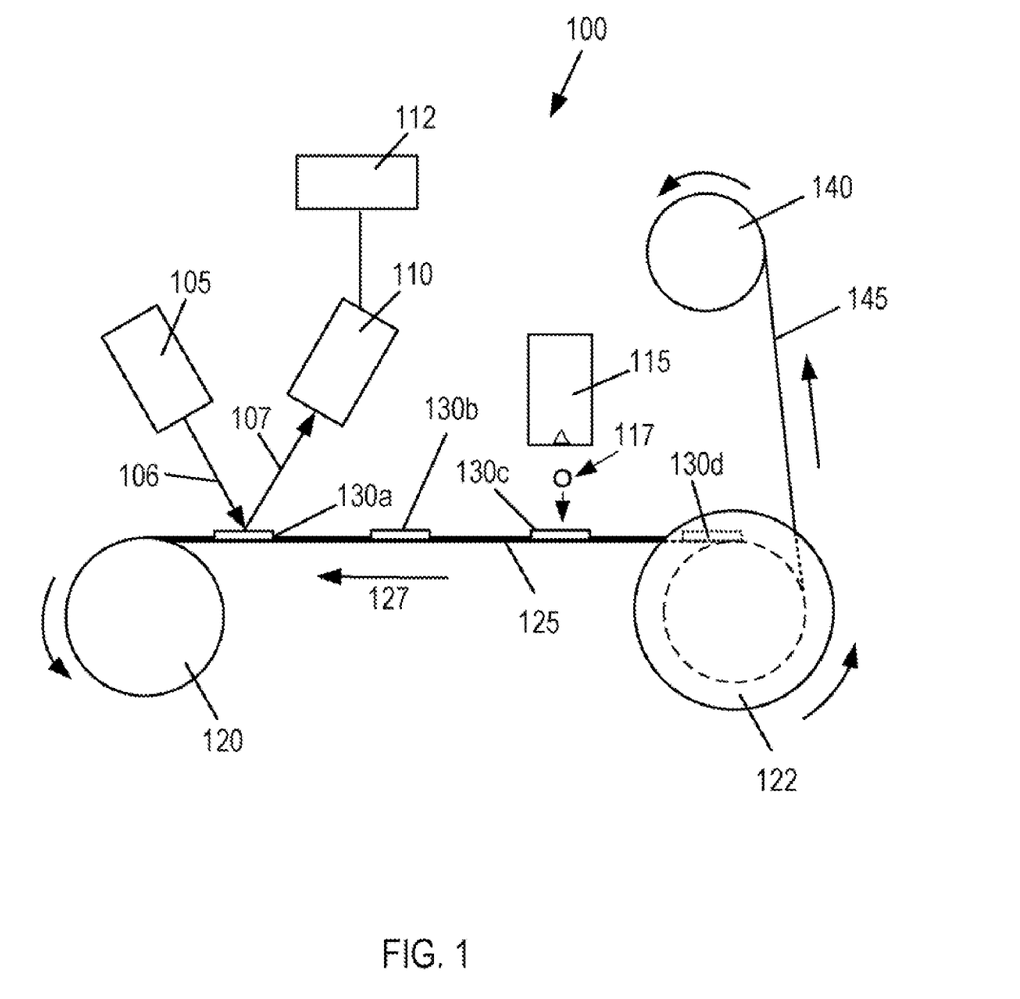
FIG. 1 is a schematic diagram of an exemplified optical sensing system for detecting chemicals and biological agents.

Referring to FIG. 1, an exemplified optical sensing system 100 includes a light source 105, a photo detector 110, an analyzer 112, and a sample collector 115. A flexible substrate 125 carrying a plurality of optical sensors 130a-130d is wound around a supply roller 122. The optical sensors 130a-130d can be sealed by a flexible sheet 145. A take-up roller 120 can move a flexible substrate 125 from a supply roller 122 in a direction 127. A driving mechanism (not shown) can rotate the take-up roller 120 to unwind the flexible substrate 125 from the supply roller 122 and to move under the sample collector 115, the light source 105, and the photo detector 110. When pulled by a roller 140 that is rotated by another or the same driving mechanism (not shown), the flexible sheet 145 is peeled off from the optical sensors 130a-130d.

The sample collector 115 can collect a chemical or biological sample in a fluid form such as a liquid, a gas or vapor, a sol gel, an aerosol, or a mixture of liquid, sol gel, gas, or vapor, and aerosol. The sample collector 115 can deliver the sample to the optical sensors 130a-130d as they are moved with the flexible substrate 125 under the sample collector 115. For example, the sample collector 115 can be a fluidic delivery device that delivers a fluid drop 117 containing the sample onto the optical sensor 130c.

The light source 105 can be a laser device configured to emit a laser beam. The photo detector 110 is configured to analyze the spectrum of a scattered light 107 from the optical sensor 130a to determine chemical content. Examples for the photo defector 110 include a UV-VIS-NIR spectrometer, Raman Spectrometer, Fourier transform infrared (FTIR) Spectrometer or fluorescence (FL) spectrometer, etc. The scattered light 107 can also include light transmitted through or emitted by the surface structures on the optical sensor 130a. The optical sensors 130a-130d and the photo detector 110 are also compatible with surface-enhanced infrared absorption, fluorescence sensing, and photoluminescence sensing.

As the optical sensor 130a moves under the light source 105 and the photo detector 110, the light source 105 emits an incident light beam 106 to illuminate the surfaces of the optical sensor 130a. The scattered light 107 from the surfaces adsorbed with the sample molecules in the optical sensor 130a is collected by the photo defector 110. The photo detector 110 can produce a spectral signal of a chemical or biological sample in response to the scattered light 107. The analyzer 112 can determine the chemical content by comparing the spectral signal from the photo detector 110 to the spectral characteristics of known chemicals. In some embodiments, the sample collector 115 can include a chemical separation device which can separate molecules in a mixture of molecules in the collected sample. Examples of a chemical separation device include gas chromatography (GC) or a high-performance liquid chromatography (HPLC).

The signal intensity in the scattered light is dependent on the coupling between the photons in the incident light beam and electrons in the chemical molecules adsorbed at the illuminated surface of the optical sensor. Such coupling can determine the electronic excitations in the adsorbed molecules and light emission from the excited electrons. The coupling among photons, electrons and phonons can be enhanced by surface structures that can induce the resonance in the excited electrons near the surfaces. Such surface structures can be characterized by dimensions that match the mean free paths (MFP) of the excited electrons, and/or wavelength of the excited electrons. For an incident laser beam having wavelengths in a range of 200 to 12,000 nanometers, the electrons' MFP can be in the range of a few nanometers to tens of nanometers. Similarly, the signal intensity in the scattered light can also depend on the coupling among the electrons, the photons and the phonons excited by the photons in the solid portions of the surface structures in the optical sensor. Similar to the excited electrons, the phonon—electron-photon coupling can also have enhanced by characteristic dimensions in the surface structures that can enable resonance of the phonons.

In accordance to the present specification, several difficulties have been encountered in using surface structures to enhance the couplings of photons with excited electrons and excited phonons. First, the MFPs for the excited electrons and the resonance wavelengths of the electrons and phonons are distributed in a range, instead of at specific fixed lengths. Secondly, the characteristic lengths may vary according to the type of molecules adsorbed to the surfaces of the optical sensor. Different molecules adsorbed on the surfaces of the optical sensor can interact with the incident light beam or the scattered lights differently, which can lead to variability in the characteristic lengths and thus affect the signal intensity in the scattered light.

Figure 2A:
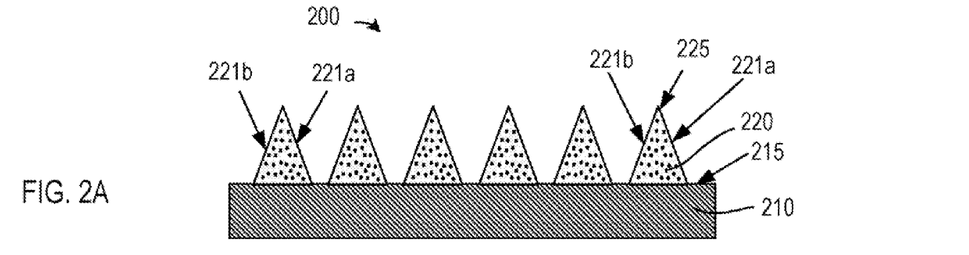
FIG. 2A is a cross-sectional view of an exemplified optical sensor compatible with the optical sensing system in FIG. 1.
Figure 2B:
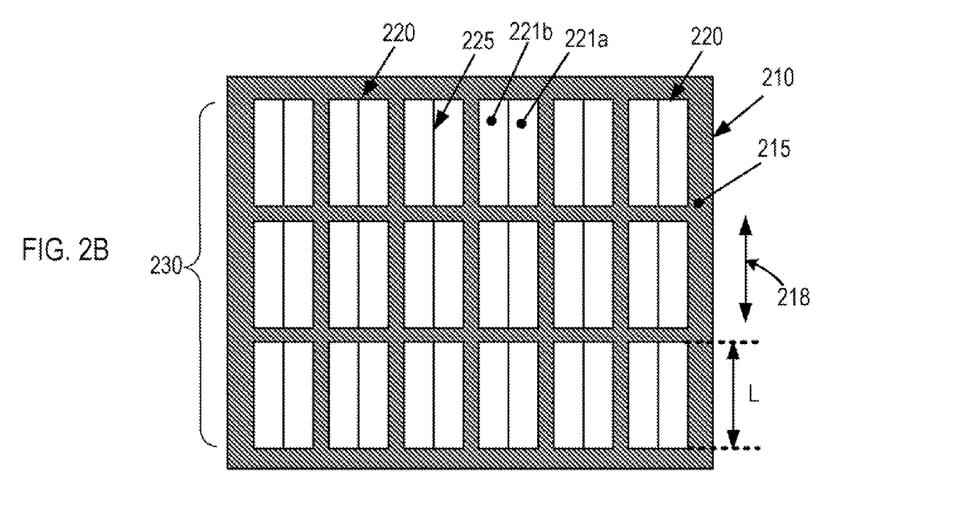
FIG. 2B is a top view of the optical sensor in FIG. 2A.
Figure 2C:
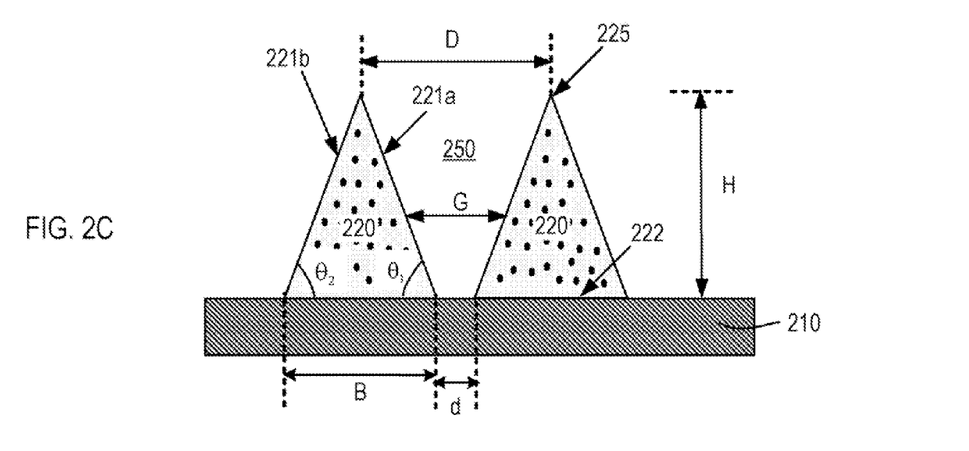
FIG. 2C is an enlarged cross-sectional view of tapered walls in the optical sensor in FIG. 2A.

In the present specification, the disclosed optical sensors are designed to maximize the couplings among the photons, the excited electrons, and phonons to enhance the signal intensity in the scattered light. The disclosed optical sensors can also increase signal intensities for a wide range of chemical samples. Referring to FIGS. 2A-2C, an exemplified optical sensor 200 includes a substrate 210, and a plurality of tapered walls 220 on the substrate 210. The substrate 210 can comprise metals, oxides, chlorine contained materials and polymer materials such as Ag, Au, Cu, Al, Fe, Co, Ni, Ru, Rh, Pd, Pt, and Cd, $TiO_2$, $SiO_2$, $Al_2O_3$, $Si_3N_4$, $Ta_2O_5$, Zn oxide, Cd oxide, Sn oxide, Sb oxide, Ag oxide, Au oxide, Ag doped with chlorine or chloride and Au doped with chlorine or chloride, or polymeric materials, such as Ethylene Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP), etc.

Figure 3A:
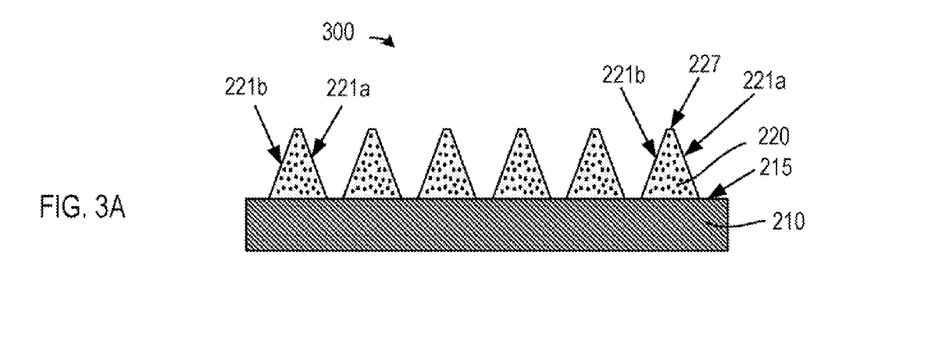
FIGS. 3A-3D are cross-sectional views of exemplified optical sensors compatible with the optical sensing system in FIG. 1.

A tapered wall 220 includes a base surface 222 having a width "B". The tapered wall 220 can be formed on an upper surface 215 of the substrate 210 or formed as an integrated structure as the substrate 210. The tapered wall 220 includes at least one sloped surface 221a or 221b. The sloped surfaces 221a and 221b are oriented at oblique angles $\theta_1$ or $\theta_2$ relative to the surface normal 215 of the substrate 210. The oblique angles $\theta_1$ or $\theta_2$ can be in a range from about 5 degrees to about 85 degrees, or from about 10 degrees to about 80 degrees, respectively. The oblique angles $\theta_1$ and $\theta_2$ can be different. The oblique angles $\theta_1$ and $\theta_2$ can also be substantially the same forming a symmetric tapered wall 220. The oblique surfaces 221a, 221b define a top portion at the top of the tapered wall 220. The top portion can include a flat top surface 227, as shown in FIG. 3A. The top surface 227 can be substantially parallel to the upper surface 215. The oblique surfaces 221a, 221b can also intersect to form a ridge 225, as shown in FIGS. 2A-2C and 3B-3C. The ridge 225 can be substantially parallel to the upper surface 215 The heights "H" of the tapered wall 220 can be in a range of about 0.5 nanometers and about 200 micrometers. The base "B" of the tapered wall 220 can be in a range of about 1 nanometer and about 200 micrometers. The lengths "L" of the tapered wall 220 can be in a range of about 2 nanometers and about 500 millimeters.

Referring to FIGS. 2B and 2C, the plurality of tapered walls 220 on the substrate 210 can be distributed in an array 230. In one arrangement, the tapered walls 220 can be disposed in a two-dimensional periodic pattern, quasi-periodic, or non-periodic pattern. In the plane of the upper surface 215 of the substrate 210, each tapered wall 220 can include a longitudinal direction 218 and a lateral direction perpendicular to the longitudinal direction 218. The ridge 225 of that tapered wall 220 is along the longitudinal direction 218.

Figure 3B:
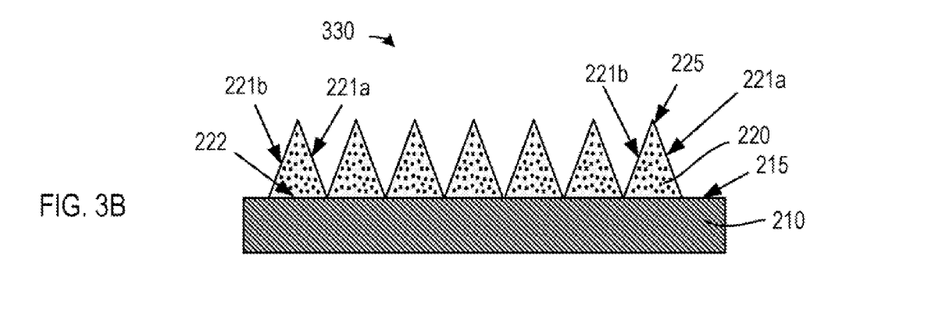

The ridges 225 of adjacent tapered walls 220 can be substantially parallel with each other along a common longitudinal direction 218. The ridges of adjacent tapered walls 220 can be separated by a distance "D" between 2 nanometers to 200 micrometers. The bases 222 of the adjacent tapered walls 220 can have a distance "d" smaller than 200 micrometers. In some embodiment, as shown in FIG. 3B below, the bases 222 of the adjacent tapered walls 220 in an exemplified optical sensor 330 can be in contact or joining with each other, that is, d=0. An air gap 250 is thus formed between two adjacent tapered walls 220. The air gap has a width varying as a function of height, ranging from "d" at the base 222 to "D" at the height of the ridges 225. The sloped surfaces 221a, 221b on the adjacent tapered walls 220 define air gaps 250. The air gap 250 has a varying width G between the sloped surfaces in the two adjacent tapered walls 220. G varies in the range from "d" to "D", i.e., d≦G≦D (FIG. 2C).

Figure 3C:
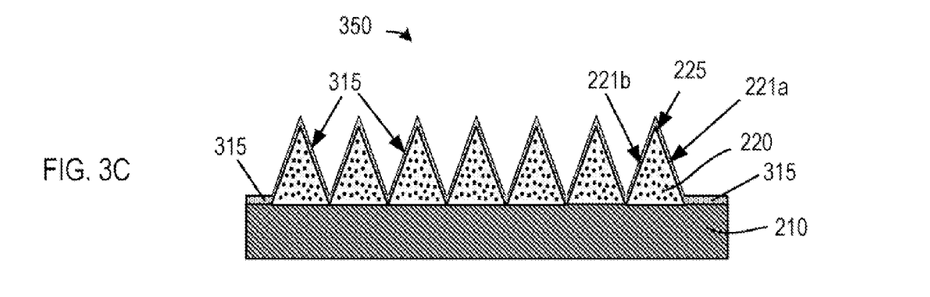

An optical sensor 350, referring to FIG. 3C, includes a conductive layer 315 formed on the sloped surfaces 221a, 221b on the tapered walls 220 and the substrate 210. The conductive materials at surfaces can help to enhance signal intensity in the scattered light 107 in certain optical sensing techniques such as Raman scattering or Surface-Enhanced Raman Scattering. Materials suitable for the conductive layer 315 include Ag, Au, Cu, Pt, Al, Fe, Co, Ni, Ru, Rh, and Pd; Ag doped with chlorine or chloride and Au doped with chlorine or chloride and conductive oxides. The thickness of the conductive layer 315 can be in the range of 0.5 nanometers-50 microns.

Figure 3D:
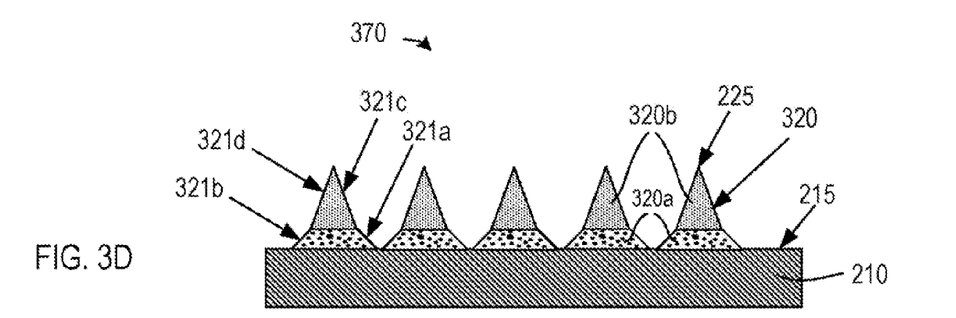

The sloped surface 221a and 221b can be substantially flat roughened, or curved. Referring to FIG. 3D, an optical sensor 370 includes a plurality of tapered walls 320 on a substrate 210. A tapered wall 320 can include a lowered portion 320a on the substrate 210 and an upper portion 320b on the lower portion 320a. The upper portion 320b can include a ridge 225. The lower portion 320a includes sloped surface 321a and 321b. The upper portion 320b includes sloped surface 321c and 321d. The sloped surfaces 321a, 321c have different slopes. The sloped surfaces 321b, 321d have different slopes.

Figure 4A:
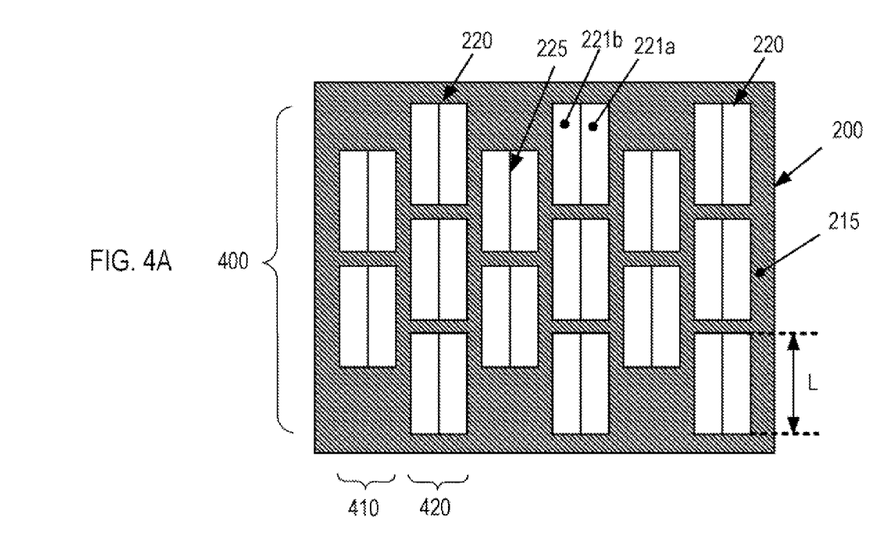
FIG. 4A is a top view of another exemplified optical sensor compatible with the optical sensing system in FIG. 1.
Figure 4B:
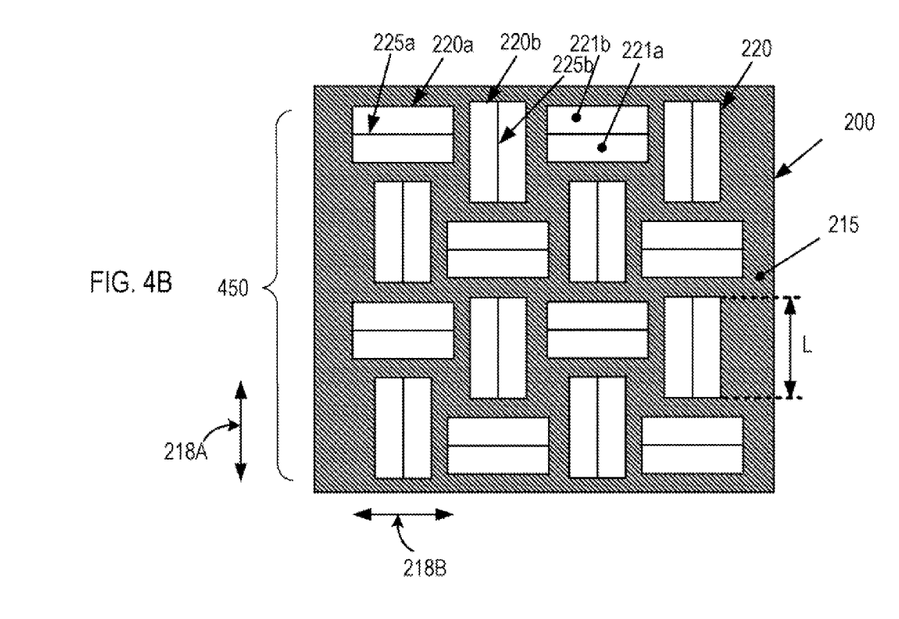
FIG. 4B is a top view of another exemplified optical sensor compatible with the optical sensing system in FIG. 1.

The tapered walls 220 can be distributed in different patterns on the substrate 210. In an array 400 of the tapered walls 220, as shown in FIG. 4A, tapered walls 220 in the adjacent columns 410, 420 can be located in offset positions relative to each other. The ridges 225 of the tapered walls 220 can be substantially parallel to each other in the array 230 (shown in FIGS. 4A and 2B). The tapered walls 220 can also be distributed at slanted angles relative to each other. An array 450, as shown in FIG. 4B, includes adjacent tapered walls 220a, 220b whose respective ridges 225a, 225b are approximately perpendicular to each other. The two sets of orthogonally aligned tapered walls 220a, 220b can thus define a common longitudinal direction 218A and a common longitudinal direction 218B respectively. In some embodiments, the tapered walls 220 can be characterized by a periodic pattern of unit cells each comprising one or more tapered walls 220. The unit cells can have rectangular, square, hexagonal, polygonal, oval, circular, triangular, and other shapes. For example, the optical sensor shown in by FIG. 4B can be viewed as formed by unit cells each comprising four adjacent tapered walls 220 that are positioned along the four sides of a square. A polygon-shaped unit cell can have its sides parallel to the longitudinal direction 218

The disclosed optical sensors include several advantageous features that can improve the performance of an optical sensing system, based on the disclosed optical, sensors. Referring to FIGS. 2A-2C, sample molecules are adsorbed on the surfaces (including the sloped surfaces 221a, 221b) of the tapered walls 220. Electrons can be excited in the air gaps 250 between the tapered walls 220. Phonons can be excited in the tapered walls 220 and the substrate 210. The varying widths G at different heights in the air gap 250 provide different resonance dimensions for the excited electrons between the tapered walls 220. Excited electrons having a range of MFPs and wavelengths can thus be strongly coupled with the incident, photons and produce localized surface resonance, thus producing increased intensity in the scattered light (or emitted light). Similarly, the tapered walls 220 also include varying widths from their bases 222 to their perspective ridges 225, which allow the incident, photons to be strongly coupled to excited phonons having different wavelengths. The varying dimensions within and between the tapered walls 220 in the planar directions of the substrate 210 can also provide appropriate resonance lengths for excited phonons and excited electrons in the presence of different molecules adsorbed on the surfaces. As a result, a wide range of sample chemicals can be detected by a single optical sensor.

Another advantageous feature of the above disclosed optical sensors is that they allow further optimization of the interaction between incident light beam and the surface structures. The direction and polarization angle of the incident light can be optimized to increase the coupling between the photons and the excited electrons and/or phonons on the surfaces to increase the intensity of the scattered signal. Referring to FIGS. 1, 5A-6B, an incident light beam 106 emitted by a light source 105 impinges on the tapered walls 220 at an incident angle "q" relative to the upper surface 215 of the substrate 210. the range of q is from 5 degree to 90 degree. The incident light beam 106 can be decomposed into a component 106n normal to the upper surface 215, and a component 106t tangential (or parallel) to the upper surface 215. The component 106t is thus a projection of the incident light beam 106 in the plane of the upper surface 215. The incident light beam 106 can be aligned such that its tangential component 106t is substantially perpendicular to, parallel to, or to the angle in between to the tapered walls 220 (and their associated ridges 225) on the substrate 105. In some embodiments, the incident light, beam 106 can be aligned substantially perpendicular to the sloped surface 221a or 221b. In other words, the sum of the angle "q" and the oblique angles $\theta_1$ or $\theta_2$ is approximately 90 degrees.

Figure 5A:
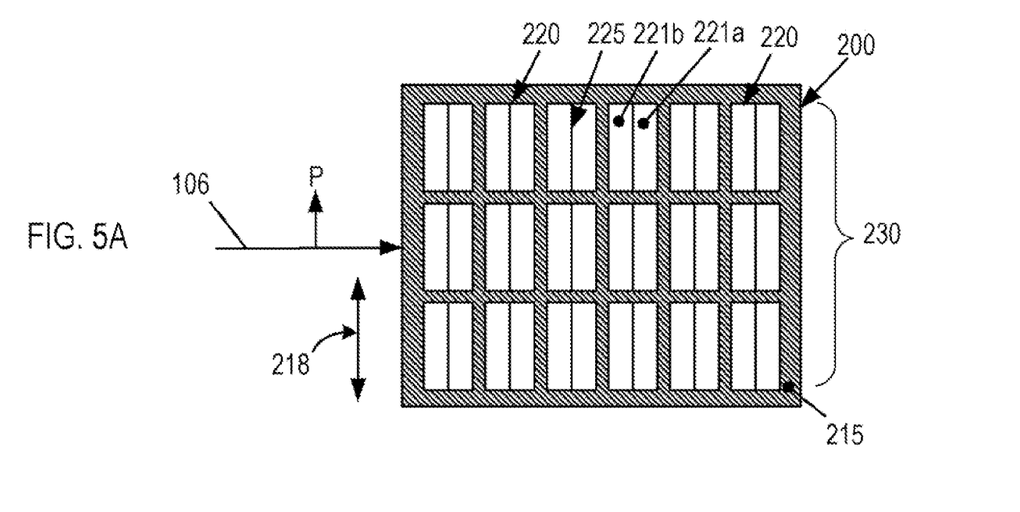
FIG. 5A is a schematic top view illustrating exemplified relative configurations of an optical sensor and an incident light beam compatible with the optical sensing system in FIG. 1.
Figure 5B:
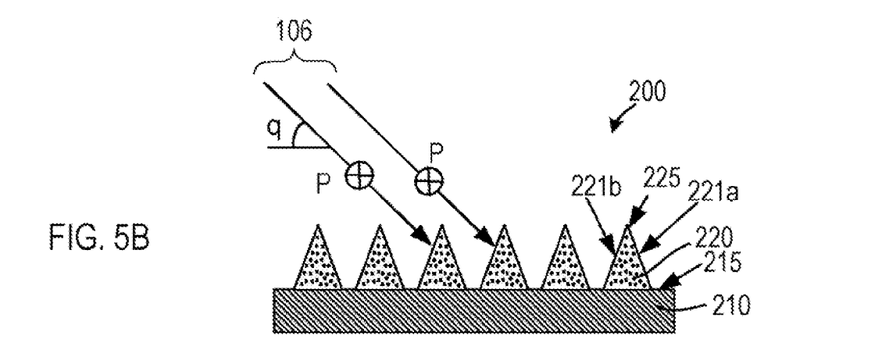
FIG. 5B is a schematic cross-sectional view illustrating exemplified relative configurations of an optical sensor and an incident light beam compatible in FIG. 5A.
Figure 5C:
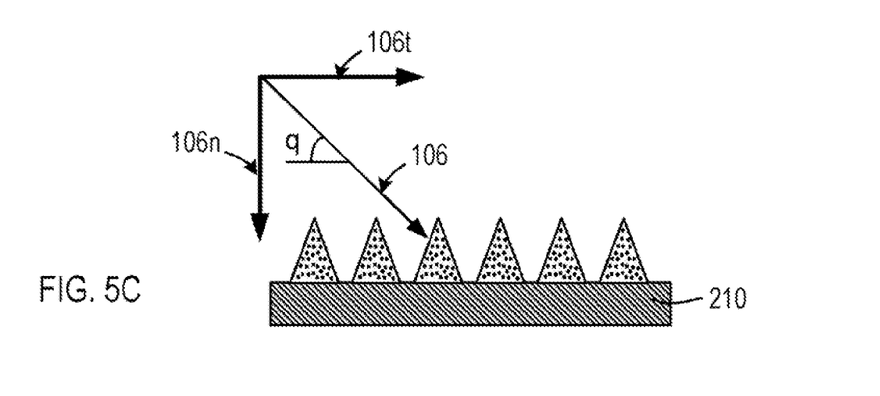
FIG. 5C is a schematic cross-sectional view showing the vector components of the incident light beam relative to the upper surface of the substrate in FIG. 5A.
Figure 6A:
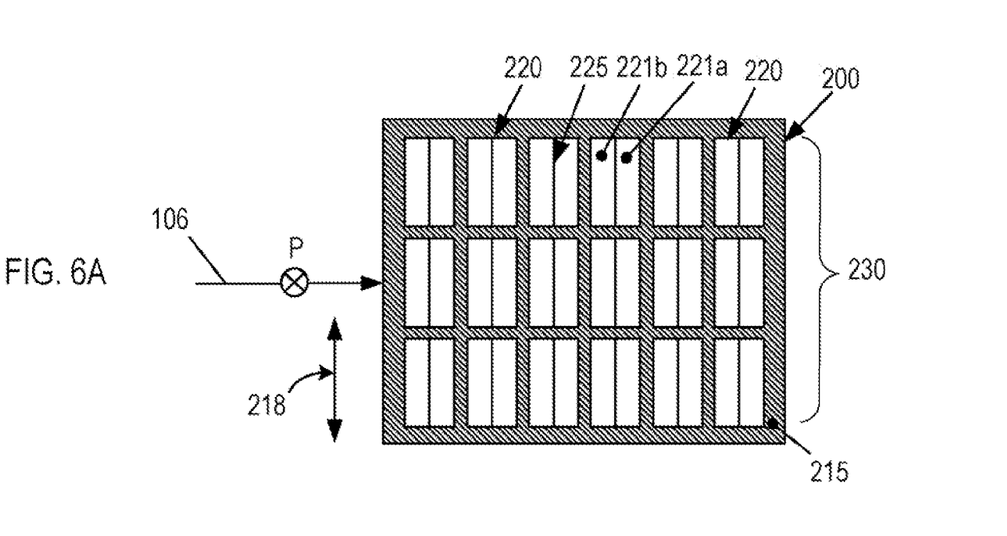
FIG. 6A is a schematic top view illustrating other exemplified relative configuration between an optical sensor and an incident light compatible with the optical sensing system in FIG. 1.
Figure 6B:
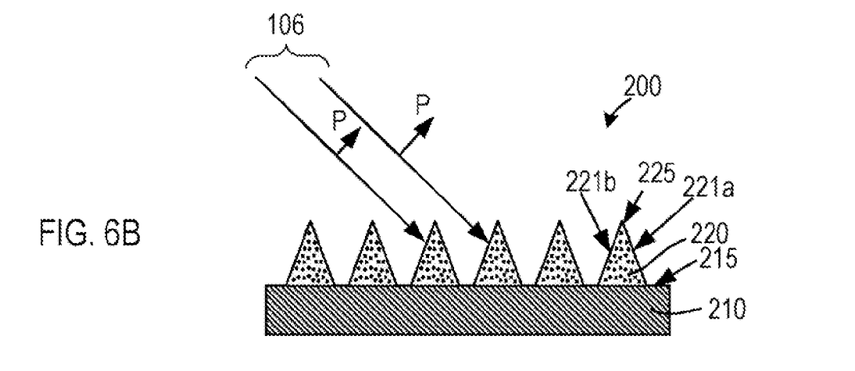
FIG. 6B is a schematic cross-sectional view illustrating another exemplified relative configuration between an optical sensor and an incident light compatible in FIG. 6A.

The incident light beam 106 can be linearly or circularly polarized. For instance, a linearly polarized incident light beam 106 can have its polarization substantially parallel to the longitudinal direction 218 of the tapered walls 220, as shown in FIGS. 5A-5B. In an implementation, the tapered walls 220 in the optical sensor 200 can be substantially parallel to each other to define a common longitudinal direction 218. In another example, a linearly polarized incident light beam 106 can have its polarization substantially perpendicular to the longitudinal direction 218 of the tapered walls 220, as shown in FIGS. 6A-6B. The linear polarization of the incident light beam 106 can also be oriented in other directions relative the upper surface 215 and the longitudinal direction 218.

Figure 7A:
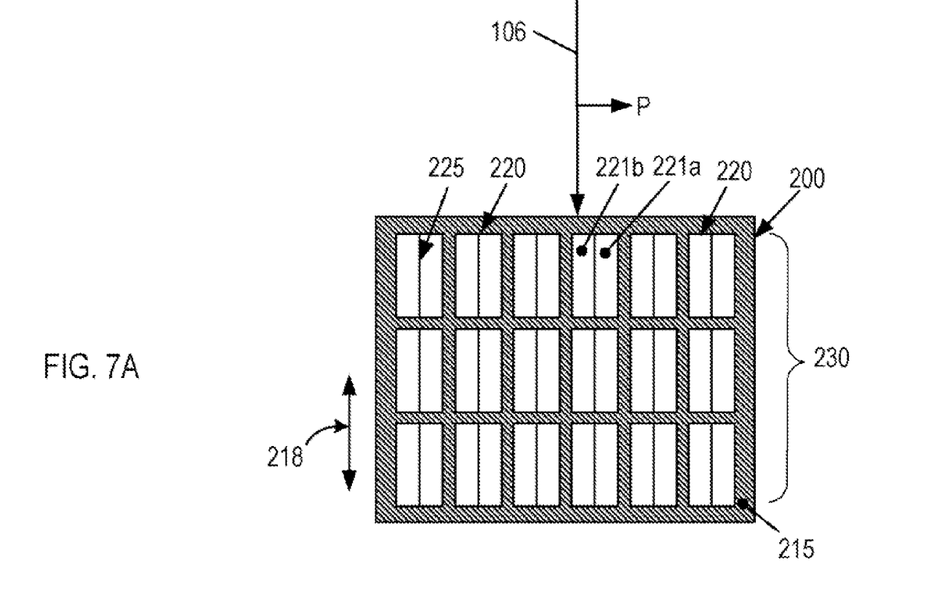
FIGS. 7A-7D are schematic top views illustrating other exemplified configurations between an incident light and an optical sensor in the optical sensing system in FIG. 1.
Figure 7B:
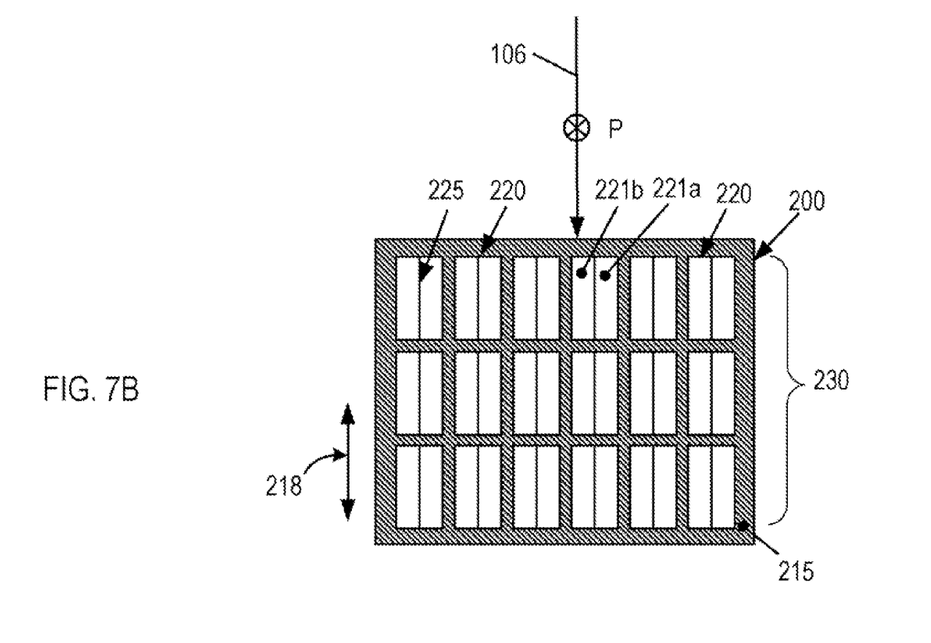
Figure 7C:
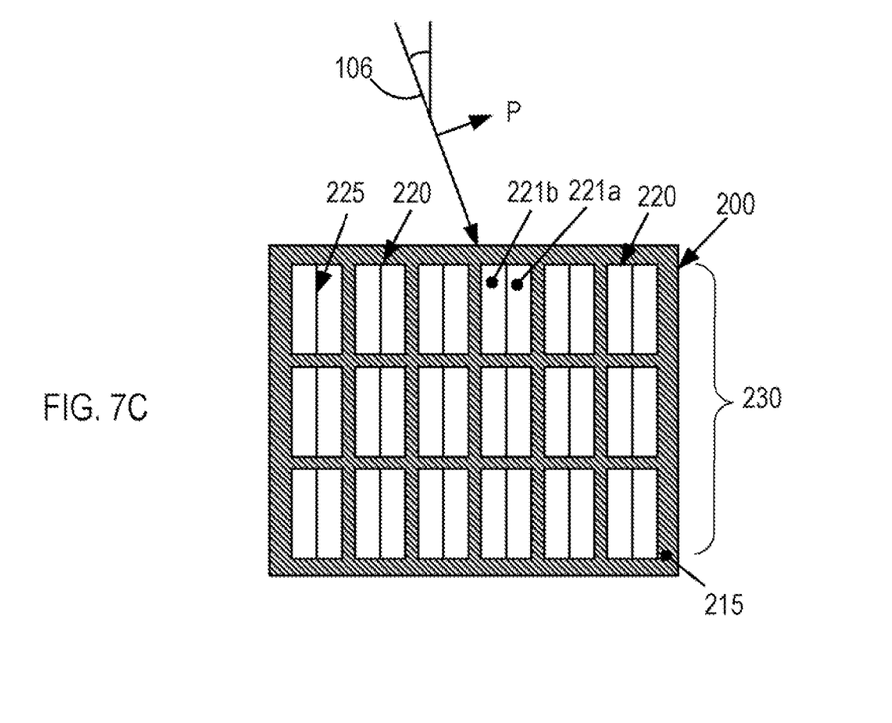
Figure 7D:
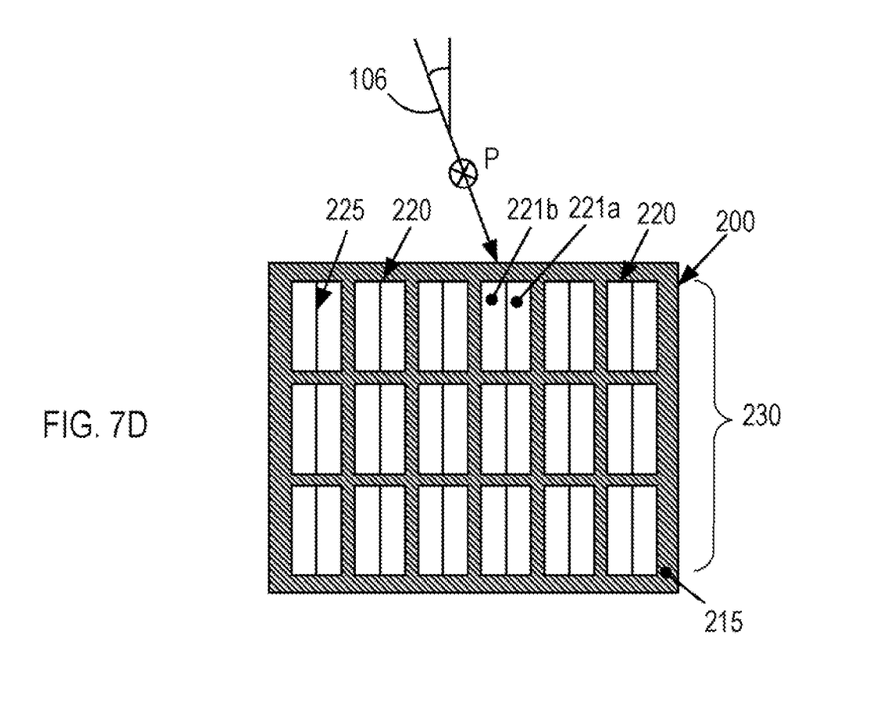

In some embodiments, the wavelength of the incident laser beam 106 can be varied such that the wavelength can best match the structural dimensions of the tapered walls 220. Exemplified wavelength range for the incident laser beam 106 is from about 200 to about 12,000 nanometers Referring to FIGS. 1, 7A-7B, an incident light beam 106 emitted by a light source 105 has its tangential component 106t. (see FIG. 5C) substantially parallels to the longitudinal direction 218 of the tapered walls 220 and another component normal to the upper surface 215 of the substrate 210. The incident light beam 106 can be linearly or circularly polarized. For instance, a linearly polarized incident light beam 106 can have its polarization substantially parallel to the upper surface 215 (and perpendicular to the longitudinal direction 218), as shown in FIG. 7A. In another example, the linearly polarized incident light beam 106 can have a polarization component orthogonal to the longitudinal direction 218, as shown in FIG. 78. The linear polarization of the incident light beam 106 can also be oriented in other directions relative the upper surface 215 and the ridges 225. In other examples, as shown in FIGS. 7C and 7D, the planar component of the incident light beam 106 is aligned at an angle "φ" in a range between 0 and 180 degrees relative to the longitudinal direction 218. A linear polarization of the incident beam 106 can also be parallel (FIG. 7C), perpendicular (FIG. 7D) or oblique to the longitudinal direction 218.

Figure 8:
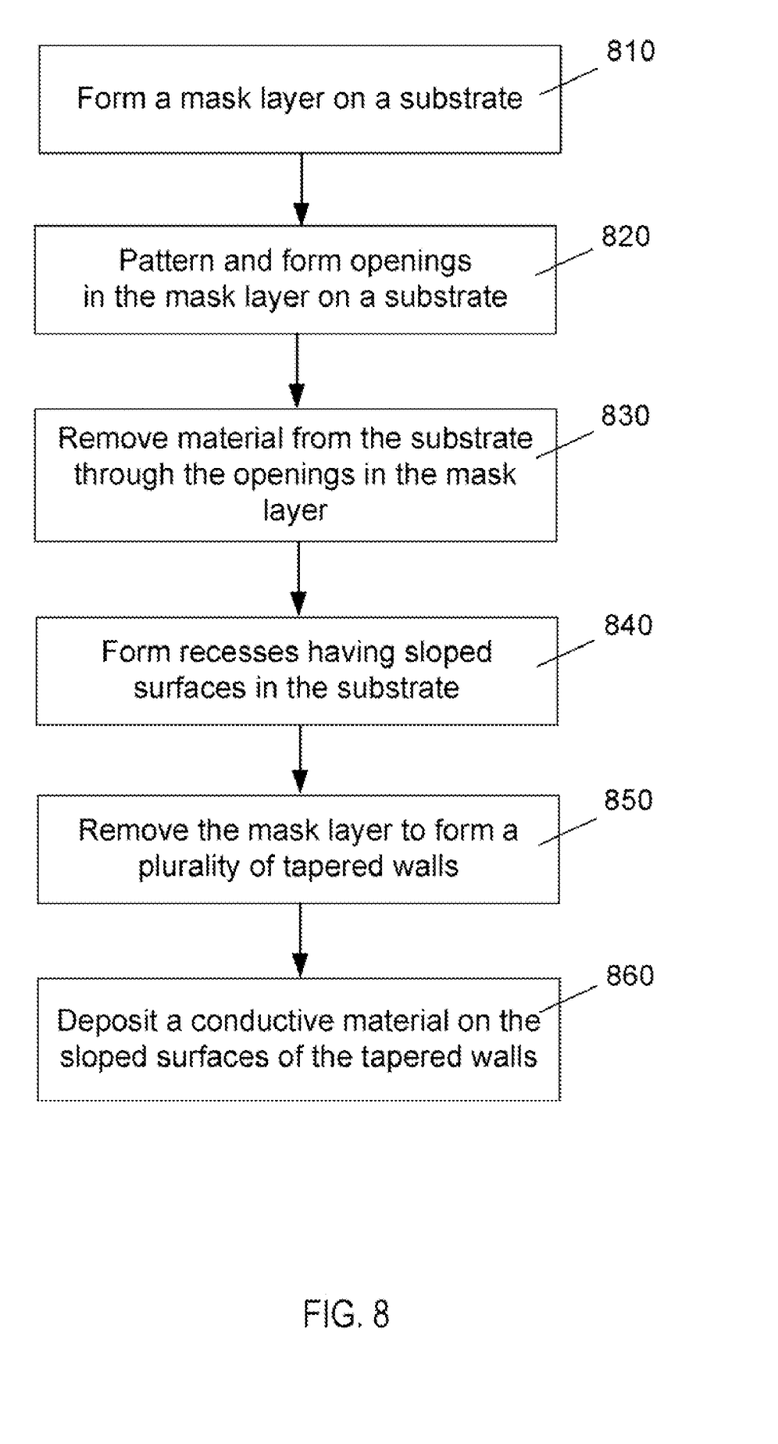
FIG. 8 is an exemplified process for fabricating the optical sensor disclosed in FIGS. 1-7B.

The disclosed optical sensor can be fabricated by different techniques. An exemplified fabrication process can include the following steps. Referring to FIG. 8, a mask layer is first formed on a substrate (step 810). The substrate can be a silicon wafer having a well defined crystallographic surface (e.g. (100) or (111) surface orientation). Multiple layers can be deposited on the surface of silicon wafer 210, which can comprise metals, oxides, chlorine contained materials and polymer materials such as Ag, Au, Cu, Al, Fe, Co, Ni, Ru, Rh, Pd, Ft, and Cd, $TiO_2$, $SiO_2$, $Al_2O_3$, $Si_3N_4$, $Ta_2O_5$, Zn oxide, Cd oxide, Sn oxide, Sb oxide, Ag oxide, Au oxide, Ag doped with chlorine or chloride and Au doped with chlorine or chloride, or polymeric materials, such as Ethylene Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP), etc. The mask layer can comprise an oxide material such as silicon oxide, aluminum oxide, etc, metal materials, such as aluminum. The mask layer is then patterned to form openings to expose some areas of the upper surface of the substrate (step 820) using techniques such as photolithography, e-bean lithography, focused-ion beam lithography, molecular imprint method, etc. The portions of the substrate under the openings in the mask layer are then directionally etched by a chemical etch ant (step 830). As a result, recesses are formed in the substrate under the openings in the mask layer (step 840). For example, if the upper surface of the substrate is a (100) crystallographic plane, the etchant can be selected to have a slow wet etching rate in the (111) direction so that sloped (111) surfaces are formed on the substrate defining the recesses. If the upper surface of the substrate is a (111) crystallographic plane, the wet etchant can be selected to have a slow etching rate in the (100) direction so that sloped (100) surfaces are formed on the substrate defining the recesses. The mask layer is then removed to form tapered wall structures on the substrate (step 850). The tapered walls may include flat top surfaces. Additional direction etching can reduce the flattop areas, which can produce narrow ridges on the tapered walls. A conductive material and oxide materials can be subsequently deposited on the tapered walls (step 860). The amount of the deposited conductive material can be controlled to optimize the thickness of the conductive layer. On the other hand, if multiple layers were deposited on the surface of a silicon wafer, a glass slice, or a thin metal plate, dry etch process can be applied through the mask to define recesses with targeted depth and side-wall slope angle. Then the mask layer can be removed thus to form taped structures on the substrate.

The disclosed systems and methods can increase the signal intensities in detecting chemicals using optical sensing techniques. The disclosed optical sensing systems and methods allow optical sensing techniques to be more widely applied in chemical detection. The disclosed system and methods can reliably detect trace amount of chemicals or biological agents in real time and in the field. The disclosed system and methods allow trace chemical detection using portable optical sensing devices, which can enable chemical detection to be conveniently implemented at locations such as security gates at airports, buildings, and cargo for detecting explosive materials and biological agents, grocery stores for monitoring food contamination, and doctors' office for diagnostic tests or medical screening test for clinic health care and medical insurance application, and inspect contamination in water and soil for environmental application. The disclosed optical sensing systems and methods can also allow the detection a number of chemicals and biological agents simultaneously using a single optical sensor.

It is understood that the disclosed optical sensing system can be implemented in different configurations and additional components. For example, the optical sensors can be transported by different mechanisms. The light source and the photo detector can be positioned in different positions relative to the optical sensors. The sample collector can deliver a sample by a liquid delivery device or by blowing a gas stream to the surfaces of an optical sensor. The incident light beam can be a laser beam that couples with surface plasma formed by excited electrons and/or resonate with excited electrons.

The optical sensor can be fabricated with different techniques from the one described above. For example, tapered wall can be formed by first mechanical stamping of a compliant layer followed by curing with UV light or heating the deformed compliant layer. The tapered walls can also be formed by directional plasma etching through a hard mask.

The tapered walls on an optical sensor can have the same shapes and sizes, or different shapes and sizes. The tapered walls can have different shapes and dimensions. The longitudinal dimension of a tapered wall can be longer than its lateral dimension, or vice versa. The projection of a tapered wall in the upper surface of the substrate can have rectangular, square, oval, circular, or polygonal shapes, or a rectangular shape having rounded corners. The tapered walls can be disposed in different patterns on a substrate. Neighboring tapered walls can, for example, positioned in a circular, elliptical, rectangular, triangular, diamond, hexagonal, and other patterns. The conductive material on the tapered walls and the substrate can include different materials from the examples described above and can include multiple layers of different conductive materials. The substrate can include a conductive layer under the tapered walls. The substrate can include a bias layer under the tapered walls for providing a voltage bias or for controlling the temperature of the substrate.

What is claimed is:

1. An optical sensing system, comprising:
   an optical sensor comprising a substrate having a substantially flat upper surface, wherein the optical sensor comprises a plurality of tapered walls protruded above the substantially flat upper surface of the substrate, wherein at least one of the tapered walls is aligned along a longitudinal direction, wherein at least one of the plurality of tapered walls comprise a lower portion having a first sloped surface relative to the upper surface and an upper portion having a second sloped surface relative to the upper surface, wherein he first sloped surface and the second sloped surface have different oblique angles relative to the upper surface of the substrate, wherein the sloped surfaces are configured to adsorb molecules of a chemical sample;
   a light source configured to emit an incident light beam to impinge the plurality of tapered walls adsorbed with molecules of the chemical sample; and
   a detector configured to collect light scattered by the plurality of tapered walls to enable a determination of the sample chemical.

2. The optical sensing system of claim 1, wherein at least two of the plurality of tapered walls are substantially parallel to each other along the longitudinal direction.

3. The optical sensing system of claim 1, wherein the incident light beam is substantially perpendicular or parallel to at least one of the sloped surfaces on the tapered walls.

4. The optical sensing system of claim 1, wherein the incident light beam is substantially perpendicular to at least one of the sloped surfaces on the tapered walls.

5. The optical sensing system of claim 1, wherein the incident light beam is at an oblique angle relative to the longitudinal direction.

6. The optical sensing system of claim 1, wherein the incident light beam has a linear polarization substantially parallel to the longitudinal direction.

7. The optical sensing system of claim 1, wherein the incident light beam has a linear polarization at an oblique angle relative to the longitudinal direction.

8. The optical sensing system of claim 1, further comprising a transport system configured to move the optical sensor to a position to allow the incident light beam to impinge on the plurality of tapered walls.

9. The optical sensing system of claim 1, further comprising a device configured to deliver the chemical sample to the optical sensor.

10. The optical sensing system of claim 1, wherein the plurality of tapered walls in the optical sensor comprise varying dimensions matching the mean free paths or wavelength of excited electrons or the wavelength of phonons excited by the incident light beam.

11. The optical sensing system of claim 1, wherein at least two of the plurality of tapered walls have their respective bases separated by the substantially flat upper surface of the substrate.

12. The optical sensing system of claim 1, wherein at least one of the plurality of tapered walls in the optical sensor has a length between about 2 nanometers and about 100 millimeters along the longitudinal direction, a height between about 0.5 nanometers and about 200 micrometers, and a base having widths in a range of about 1 nanometer and about 200 micrometers.

13. The optical sensing system of claim 1, wherein two adjacent tapered walls have their respective top portions at a first distance between about 2 nanometers and about 200 micrometers and their respective bases at a second distance smaller than 200 micrometers.

14. The optical sensing system of claim 1, wherein the second sloped surface has a steeper oblique angle than the second sloped surface relative to the substantially flat upper surface of the substrate.

15. The optical sensing system of claim 1, wherein at least two adjacent tapered walls are substantially parallel to each other and have their respective bases in contact or joining with each other.

16. The optical sensing system of claim 1, wherein the top portion in the one of the plurality of tapered walls includes a top surface substantially parallel to the substantially flat upper surface of the substrate.

17. The optical sensing system of claim 1, wherein the top portion in the one of tapered walls includes a ridge substantially parallel to the longitudinal direction.

18. The optical sensing system of claim 1, wherein the lower side of the upper portion is joined to the upper side of the lower portion in the tapered wall.

19. The optical sensing system of claim 1, wherein the substrate comprise a material selected from the group consisting of silicon, $TiO_2$, $SiO_2$, $Al_2O_3$, $Si_3N_4$, $Ta_2O_5$, Zn oxide, Sn oxide, Sb oxide, Ag oxide, Au oxide, Ethylene Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP).

20. The optical sensing system of claim 1, wherein the plurality of tapered walls comprise a conductive material on the sloped surfaces.

21. The optical sensing system of claim 20, wherein the conductive material is selected from the group consisting of Ag, Au, Cu, Pt, Al, Fe, Co, Ni, Ru, Rh, Pd, Ag doped with chlorine or chloride, and Au doped with chlorine or chloride.

* * * * *